United States Patent [19]

Fischer

[11] Patent Number: 4,941,873
[45] Date of Patent: * Jul. 17, 1990

[54] CONTROLLED DIFFUSION MEDICAMENT APPLICATOR

[75] Inventor: Dan E. Fischer, Salt Lake City, Utah

[73] Assignee: Ultradent Products, Inc., Salt Lake City, Utah

[*] Notice: The portion of the term of this patent subsequent to Mar. 25, 2003 has been disclaimed.

[21] Appl. No.: 826,274

[22] Filed: Feb. 5, 1986

Related U.S. Application Data

[63] Continuation of Ser. No. 604,029, Apr. 26, 1984, Pat. No. 4,578,055, which is a continuation of Ser. No. 60,382, Jul. 25, 1979, abandoned, which is a continuation-in-part of Ser. No. 799,168, May 23, 1977, abandoned.

[51] Int. Cl.⁵ ............................................. A61B 10/00
[52] U.S. Cl. .................................... 604/54; 604/49
[58] Field of Search .................. 604/1, 49, 2, 3, 54, 604/310, 311; 401/134, 156, 176, 182, 185, 198, 205, 209

[56] References Cited

U.S. PATENT DOCUMENTS

| | | |
|---|---|---|
| 374,026 | 11/1887 | |
| 762,603 | 6/1904 | Witkowski . |
| 833,044 | 10/1906 | Goodhugh . |
| 860,555 | 7/1907 | Middaugh . |
| 870,573 | 11/1907 | Myers . |
| 1,115,561 | 11/1914 | Northey . |
| 1,164,430 | 12/1915 | Thurman . |
| 1,245,153 | 11/1917 | Evslin . |
| 1,711,352 | 4/1929 | Jeffreys . |
| 1,711,516 | 5/1929 | Alland . |
| 2,090,354 | 8/1937 | Massman ........................ 128/269 |
| 2,100,157 | 11/1937 | Chandler . |
| 2,643,655 | 6/1953 | McKay ............................ 604/184 |
| 2,754,590 | 7/1956 | Cohen . |
| 2,902,035 | 9/1959 | Hartley ............................ 128/234 |
| 3,270,743 | 9/1966 | Gingras ........................... 128/215 |
| 3,337,095 | 8/1967 | Marbach et al. ................ 222/309 |
| 3,346,147 | 10/1967 | Higgins et al. .................. 222/326 |
| 3,462,840 | 8/1969 | Ellman ............................. 32/60 |
| 3,512,526 | 5/1970 | Fielding ........................... 128/239 |
| 3,572,337 | 3/1971 | Schunk ............................ 128/222 |
| 3,581,399 | 6/1971 | Dragan ............................. 32/60 |
| 3,587,575 | 6/1971 | Lichtenstein .................... 128/215 |
| 3,760,503 | 9/1973 | Baskas .............................. 32/17 |
| 3,894,538 | 7/1975 | Richter ............................ 128/260 |
| 3,896,552 | 7/1975 | Russell ............................. 32/34 |
| 3,910,706 | 10/1975 | DelBon . |
| 4,030,496 | 6/1977 | Stait et al. ....................... 128/215 |
| 4,143,428 | 3/1979 | Cohen .............................. 3/36 |
| 4,243,035 | 1/1981 | Barrett ............................. 128/215 |
| 4,318,403 | 3/1982 | Sneider ............................ 128/232 |
| 4,329,990 | 5/1982 | Sneider ............................ 128/239 |

Primary Examiner—Edward M. Coven
Attorney, Agent, or Firm—Workman, Nydegger & Jensen

[57] ABSTRACT

A method for using a medicament applicator having a rigid, curved delivery tube which provides controlled diffusion of medicament, as well as rigidity for burnishing of tissue and removal of coagulated blood, and maneuverability for reaching desired points of application within the mouth or within an incision. The tube is curved to a pre-determined shape, and has a small amount of padding at the delivery end. Diffusion of the medicament is controlled by a pressure-applied delivery system utilizing a syringe-plunger, a syringe-capsule-plunger, a squeeze bulb or similar device. Release of the pressure-applied delivery system immediately stops the flow of medicament.

7 Claims, 6 Drawing Sheets

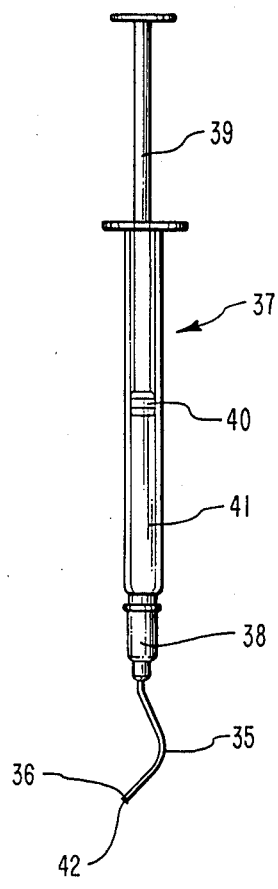
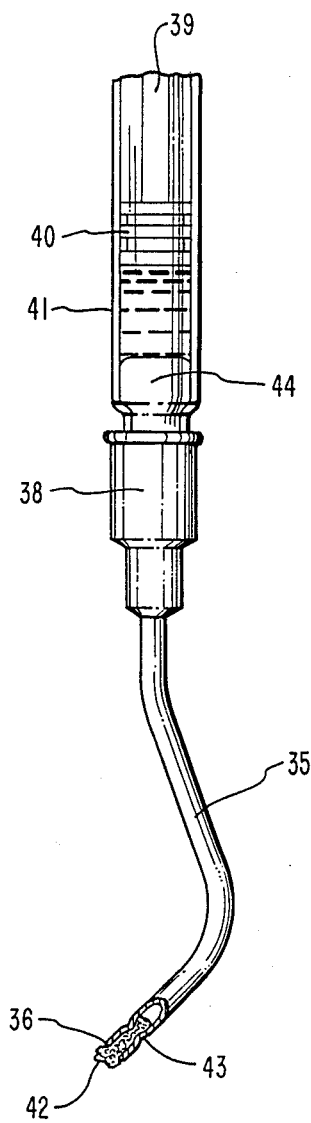
FIG. 5
FIG. 6

CONTROLLED DIFFUSION MEDICAMENT APPLICATOR

BACKGROUND OF THE INVENTION

This is a continuation of application Ser. No. 06/604,029 filed on Apr. 26, 1984, now U.S. Pat. No. 4,578,055 issued Mar. 25, 1986, which application is a continuation of application Ser. No. 06/060,382 filed on July 25, 1979, now abandoned, which application is a continuation-in-part of application Ser. No. 05/799,168 filed on May 23, 1977, now abandoned.

This invention relates to the field of fluid applicators and more specifically to medicament applicators.

Numerous devices in various forms have been developed to apply fluids to designated surfaces. The diversity of these devices range from paint brushes, quill pens, and fountain pens to felt tip pens, medicinal swabs, and power point pens. Many developments and improvements to accomplish a variety of objectives have been made. For example, in the late nineteenth century pens were developed that had internal ink reservoirs and avoided use of ink wells. Later, many devices designed to avoid leakage and terminate fluid flow to the applicator's tip were made. Applicator tips have taken a variety of forms. There are brushes, ball points, swabs, and porous textile tips to mention a few.

Despite the multitude of devices and developments, the needs of a dentist engaged in oral medicament application or a doctor engaged in delicate surgery have remained without adequate remedy. The devices that use air pressure and gravity to force capillary flow through a porous textile for a swabbing effect do not have the intricately controlled fluid flow necessary. Swab tipped devices have proved to be too large and wasteful of valuable medicaments and time. Other devices feel foreign to the dentist's or doctor's trained hand and are awkward in use.

It is an objective of the present invention to eliminate the problems recognized in the art and remedy the dentist's and doctor's needs by providing a device that is familiar in feel, can easily reach all areas within the mouth or within an incision, provides an intricate swabbing effect, and permits the dentist or doctor to control the flow of medicament in application

SUMMARY OF THE INVENTION

The medicament applicator of the invention has a syringe-type dispenser and a tube having a small amount of porous padding or filament material attached to the delivery end of the tube. The syringe type dispenser is comprised of a dispenser tube with a finger abutment cap and a plunger with a thumb disc. The tube attaches to the dispenser tube and is bent to the desired shape of a curve to accommodate access to gingival sulci, open pulp chamber, or the like, whether dental or medicinal in application. The filament or padding material protrudes slightly from the tube's end to provide a rigid swabbing effect without sharpness. This effect allows for burnishing of tissue, aids in removal of coagulated blood, and applies pressure to the tissue.

The astringent solution or other medicament is disposed within the dispenser tube. The plunger is disposed such that it slides continuously within the dispenser tube. By depressing the plunger, the medicament is forced through the tube and exudes onto the point of application. Release of the plunger creates a slight vacuum within the tube, and immediately stops the flow of medicament, thereby preventing further dispensing of medicament.

The present invention can be used in many ways with many different medicaments. It can be used to deliver astringent, hemostatic agents to a bleeding gingival sulcus prior to taking impressions, to a bleeding pulp chamber in a pulpotomy, or to a cut papilla interdentally. It can also be used to apply etching acid, such as citric or orthophosphoric acid for etching the enamel surfaces of teeth prior to resin restorations.

The present invention can be disposable or designed for office sterilization in whole or in part.

As another embodiment of the present invention, the dispenser can be designed to receive a disposable pre-filled capsule containing the desired medicament.

Another embodiment of the present invention utilizes disposable squeeze bulb instead of the syringe type dispenser. With this embodiment, the flow of medicament would be controlled by squeeze pressure between the thumb and fingers when the applicator is grasped like a pen.

THE DRAWINGS

Preferred embodiments of the invention are illustrated in the accompanying drawings, in which:

FIG. 5 is an elevational view of a preferred embodiment of the applicator; and

FIG. 6 is a partial sectional elevation of the preferred embodiment shown in FIG. 5.

DETAILED DESCRIPTION OF THE ILLUSTRATED EMBODIMENTS

Figure 1:
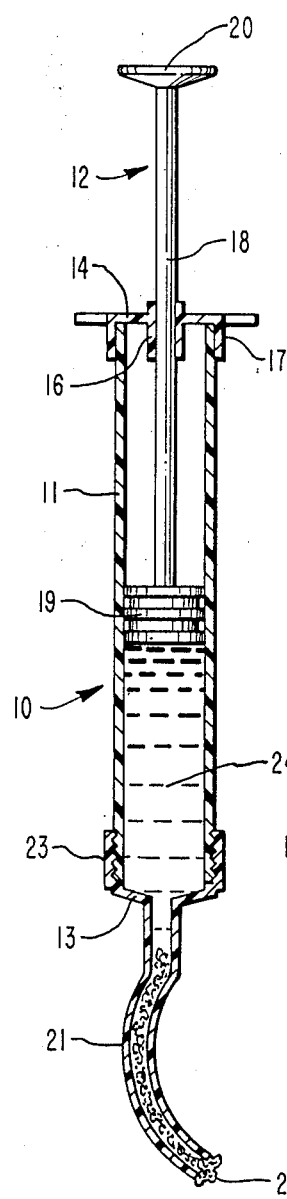
FIG. 1 is a longitudinal section of the medicament applicator.

As shown in FIG. 1, a preferred embodiment of the medicament applicator 10 is comprised of a dispenser tube 11, a plunger 12, and a detachable needle cap 13. The dispenser tube 11 is substantially cylindrical in shape, has a plunger cap 14 affixed to its lower end, and has male threads 15 grooved in its upper end or can be a Luer-Lock coupling, friction coupling or the like. It is understood that the dispenser tube 11 may be constructed with a cross section of any shape, however, circular is preferred. Said plunger cap 14 is constructed with a bore guide 16 and a finger abutment 17.

The plunger 12 is comprised of a plunger shaft 18, a stopper 19, and a thumb disc 20. Said plunger shaft 18 is disposed through the bore guide 16. Said stopper 19 has its outer edge contiguous with the inner wall of the dispenser tube 11.

The tube cap 13 has female threads 23 and a tube 21 with a preferably porous polyester cord filament 22 disposed therein. Said tube 21 is bent to any desired shape to facilitate application of a medicament 24 to difficult to reach areas within the mouth or within an incision. Said porous filament 22 protrudes slightly from the tube 21 so as to act as an intricate swab and to reduce the tube's sharpness. The filament 22 is fitted tightly enough to allow for controlled flow of medicament 24 to the tip of the tube 21. It is understood that the filament 22 may be made of any porous fiber, but polyester cord is preferred.

The dispenser tube 11 is filled with medicament 24 by removing the tube cap 13 and drawing the desired amount of said medicament 24 into said tube 11. The cap 13 is then replaced on the tube 11. By depressing the plunger 12 the medicament 24 is forced through the filament 22 and exudes onto the point of application.

The applicator 10 is constructed of easy to sterilize materials. The dispenser tube 11, plunger shaft 18, and thumb disc 20 may be constructed of glass, metal, nonporous plastic, or the like. The plunger stopper 19 may be made of a resilient rubber. The tube 21 is made of a metal so as to retain its bend and rigidity.

The medicament applicator 10 may be disposed of or office sterilized in whole or in part.

It is understood that the applicator may be designed for an air trap pump system which would deliver an even flow of medicament without constant thumb pressure after the plunger has been pumped.

Figure 2:
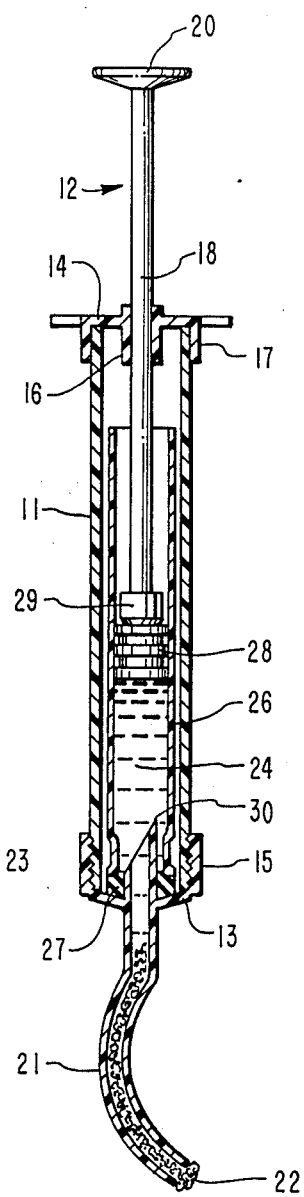
FIG. 2 is a longitudinal section of a medicament applicator adapted for capsule use with a capsule disposed therein.
Figure 3:
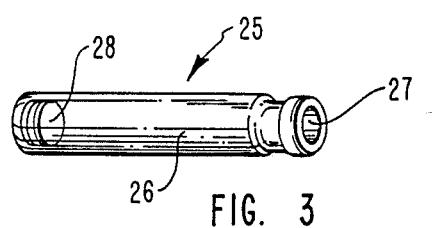
FIG. 3, is a perspective view of a medicament capsule.

Another embodiment of the present invention is illustrated in FIGS. 2 and 3. This embodiment is an adaptation for capsule use. The capsule 25 is shown in FIG. 3. Said capsule 25 is comprised of a capsule tube 26, a membrane 27, and a capsule stopper 28. The capsule 25 is shaped such that it readily fits within the dispenser tube 11. The dispenser tube 11 is the same as shown in FIG. 1. The plunger 12 is adapted to capsule use by having a rigid head 29 in place of the stopper 19. The tube cap 13 has also has one adaptation, that being a sharp inner tip 30.

The capsule 25 is inserted into the dispenser tube 11. The tube cap 13 is then attached to the dispenser tube 11. By depressing the plunger 12, the capsule 25 is pushed forward until it rests against the tube cap 13 and the sharp inner tip 30 punctures the capsule membrane 27. Further pressure on the plunger 12 causes the plunger head 29 to engage and push the capsule stopper 28 forward. The capsule stopper 28 forces the medicament 24 within the capsule 25 through the filament 22. The medicament 24 exudes from the filament 22 onto the point of application.

After use, the capsule 25 may be removed from the dispenser tube 11 and disposed of.

Figure 4:
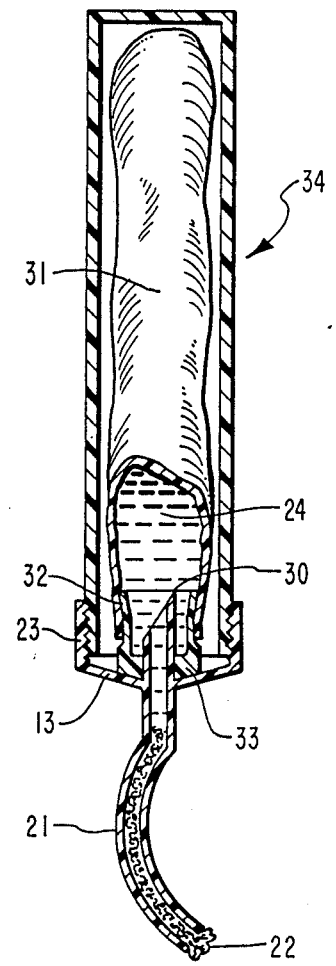
FIG. 4 is an elevational view of a squeeze bulb applicator.

Another embodiment of the present invention is illustrated in FIG. 4. The squeeze bulb embodiment utilizes a resilient squeeze bulb 31 instead of a syringe type delivery system. The squeeze bulb 31 is attached at its lower end to a metal cap 32 which has at its lower end a membrane 33 similar to the membrane described above in FIGS. 2 and 3. This membrane can be punctured by a sharp inner tip 30. In this manner, it may be easily squeezed between the thumb and fingers.

Before attaching the tube cap 13, the medicament 24 is poured into the squeeze bulb 31. The cap 13 is then attached. By squeezing the bulb 31 as described above, the medicament 24 is forced through the filament 22 and exudes onto the point of application.

Said squeeze bulb 31 is made of a resilient nonabsorbent, nonporous rubber. However, it is understood that any material having the above desired characteristics may be used.

A preferred embodiment of the invention is shown in FIGS. 5 and 6. The applicator tube 35 is of metal construction and has a curve such that the tip 36 of the tube is either on axis or slightly beyond the axis of the dispenser 37, to aid in the use of the applicator by a trained technician.

Tube 35 is attached to cap means 38 by which tube 35 is easily mounted and detached from the end of dispenser 37.

Dispenser 37 is a conventional disposable plunger-operated syringe having a plunger 39 with a plunger head 40 forming an air-tight seal with the interior of the dispenser housing 41, usually of clear plastic construction.

The tip 36 of tube 35 is provided with a small wad of porous material 42, such as a polyester filament or the like, through which the medicament can flow when pressure is applied to plunger 39. Preferably, material 42 extends only a short distance into the tip of tube 35 and may be held in position by crimping the tube 35 on both sides 43. The purpose of material 42 is to provide a burnishing action on the afflicted area, and to control the flow of medicament through tube 35. Material 42 provides some back pressure against the positive pressure of plunger 39, so as to help regulate the flow of medicament.

When the pressure is removed from the plunger 39, the backpressure of material 42 in place in the tip of tube 35 creates a slight vacuum in the form of an air bubble 44 within the applicator to prevent the further dispensing of medicament from the applicator.

It is to be understood that the particular forms of the invention described herein and illustrated in the accompanying drawings are preferred embodiments. Various changes in shape, size, materials, and arrangement of parts may be made without departing from the spirit of the invention as defined in the attached claims.

I claim:

1. A method for controlling bleeding during dental procedures using a medicament applicator, said medicament applicator comprising a chamber containing a coagulant under pressure connected to a hollow tube having a padded orifice through which the coagulant is dispensed under hydraulic pressure, the method comprising the steps of:

applying under hydraulic pressure a coagulant to a desired area of gingival tissue using the medicament applicator so as to infuse coagulant into exposed capillaries of such tissue such that the blood within said capillaries becomes coagulated; and simultaneously rubbing the tissue with said medicament applicator in order to remove any coagulated blood existing on the surface of the gingival tissue so as to substantially prevent reinitiation of bleeding.

2. A method for controlling bleeding during dental procedures using a medicament applicator as defined in claim 1 wherein the step of applying under hydraulic pressure a coagulant to the gingival tissue further comprises providing sealing engagement of the padded orifice of the applicator with the gingival tissue sufficient to cause some back pressure against the coagulant under pressure in the hollow tube of the applicator, thereby regulating the infusion of the coagulant into the exposed capillaries of the gingival tissue.

3. A method for infusing controlled amounts of a hermostatic agent into gingival tissue of a patient during dental procedures, the method comprising the steps of:

providing an applicator capable of controlled dispensing of a hemostatic agent under pressure through a porous surface of the applicator;

placing the porous surface of the applicator against the gingival tissue in order to provide sealing engagement of the porous surface of the applicator with the gingival tissue sufficient to cause some back pressure against the pressure of the hemostatic agent being dispensing by the applicator, thereby regulating the flow of the hemostatic agent through the applicator;

infusing the hemostatic agent into the gingival tissue under pressure; and mechanically burnishing the surface of the gingival tissue by moving the porous surface of the applicator while said porous surface is in contact with the gingival tissue thus removing coagulum from the surface of the gingival tissue.

4. A method for infusing controlled amounts of a hemostatic agent to cut live gingival tissue of a patient during dental procedures, the method comprising the steps of:

providing an applicator capable of controlled dispensing of a hemostatic agent by hydraulic pressure through a porous surface of the applicator;

placing the porous surface of the applicator against the cut live gingival tissue of the patient;

infusing under pressure the hemostatic agent into the openings of the capillaries of the cut live gingival tissue such that hemostasis occurs in the orifices of the capillaries; and burnishing the gingival tissue with the porous surface of the applicator so as to remove coagulated blood on the surface of the gingival tissue of the patient.

5. A method as defined in claim 4 wherein the step of burnishing the tissue further comprises providing sealing engagement of the porous surface of the applicator with the tissue of the patient sufficient to cause some back pressure against the hydraulic pressure provided by the applicator.

6. A method as defined in claim 4, wherein the tissue is simultaneously burnished with the porous surface of the applicator while the hemostatic agent is infused into the tissue by hydraulic pressure.

7. A method as defined in claim 5 wherein the tissue is simultaneously burnished with the porous surface of the applicator while the hemostatic agent is infused into the tissue by hydraulic pressure.

* * * * *

UNITED STATES PATENT AND TRADEMARK OFFICE
CERTIFICATE OF CORRECTION

PATENT NO. : 4,941,873

DATED : July 17, 1990

INVENTOR(S) : DAN E. FISCHER

It is certified that error appears in the above-identified patent and that said Letters Patent is hereby corrected as shown below:

Title page, column 1, lines 1-2, "CONTROLLED DIFFUSION MEDICAMENT APPLICATOR" should be --METHODS FOR CONTROLLED DIFFUSION MEDICAMENT APPLICATION--

Column 1, line 45, after "application" insert --.--
Column 2, line 37, after "elevation" insert --view--
Column 2, line 51, "circular is preferred." should be --a circular shape is preferred.--
Column 3, line 44, after "and" insert --may be--
Column 4, line 7, after "usually" insert --comprised--
Column 5, line 3, "being dispensing" should be --being dispensed--

Signed and Sealed this

Thirteenth Day of October, 1992

Attest:

DOUGLAS B. COMER

*Attesting Officer*  Acting Commissioner of Patents and Trademarks